United States Patent
Yamamoto (10) Patent No.: US 10,898,078 B2
(45) Date of Patent: Jan. 26, 2021

(54) PHOTOACOUSTIC IMAGE GENERATION METHOD AND APPARATUS

(71) Applicant: FUJIFILM Corporation, Tokyo (JP)

(72) Inventor: Hiroaki Yamamoto, Ashigarakami-gun (JP)

(73) Assignee: FUJIFILM Corporation, Tokyo (JP)

( * ) Notice: Subject to any disclaimer, the term of this patent is extended or adjusted under 35 U.S.C. 154(b) by 527 days.

(21) Appl. No.: 15/464,873

(22) Filed: Mar. 21, 2017

(65) Prior Publication Data
US 2017/0188838 A1    Jul. 6, 2017

Related U.S. Application Data (63) Continuation of application No. PCT/JP2015/004415, filed on Aug. 31, 2015.

(30) Foreign Application Priority Data

Sep. 24, 2014 (JP) ................ 2014-193566

(51) Int. Cl.
*A61B 5/00* (2006.01)

(52) U.S. Cl.
CPC ............ *A61B 5/0095* (2013.01); *A61B 5/742* (2013.01)

(58) Field of Classification Search
CPC ........................ A61B 5/0095; A61B 5/742
See application file for complete search history.

(56) References Cited

U.S. PATENT DOCUMENTS

| 2005/0004458 A1 | 1/2005 | Kanayama et al. |
| 2005/0187471 A1 | 8/2005 | Kanayama et al. |
| 2012/0296192 A1 | 11/2012 | Fukutani |
| 2013/0245419 A1 | 9/2013 | Oishi |

FOREIGN PATENT DOCUMENTS

| JP | 2005-21380 A | 1/2005 |
| JP | 2005-218684 A | 8/2005 |
| JP | 2008-284329 A | 11/2008 |
| JP | 2011-217767 A | 11/2011 |
| JP | 2012-231879 A | 11/2012 |

(Continued)

OTHER PUBLICATIONS

Japanese Notification of Reasons for Refusal, dated Jan. 30, 2018, for corresponding Japanese Application No. 2016-549915, with an English machine translation.

(Continued)

*Primary Examiner* — Michael T Rozanski
(74) *Attorney, Agent, or Firm* — Birch, Stewart, Kolasch & Birch, LLP

(57) ABSTRACT

In a photoacoustic image generation apparatus for obtaining a photoacoustic signal by emitting light toward a subject from a light source and detecting photoacoustic waves emitted from the subject having received the light and imaging the subject based on the photoacoustic signal, there are provided: means for removing a signal showing a component appearing discontinuously in the subject from photoacoustic signals relevant to a plurality of cross sections of the subject that have been generated by changing an angle between an emission direction of the light and a surface of the subject; and means for constructing a three-dimensional image of the subject from photoacoustic signals showing the plurality of cross sections after the removal processing.

5 Claims, 5 Drawing Sheets

(56) References Cited

FOREIGN PATENT DOCUMENTS

| | | |
|---|---|---|
| JP | 2013-128760 A | 7/2013 |
| JP | 2013-188310 A | 9/2013 |

OTHER PUBLICATIONS

International Search Report, issued in PCT/JP2015/004415 (PCT/ISA/210), dated Dec. 22, 2015.
Written Opinion of the International Searching Authority, issued in PCT/JP2015/004415 (PCT/ISA/237), dated Dec. 22, 2015.
Japanese Office Action dated Apr. 17, 2018 for corresponding Japanese Application No. 2016-549915, with English machine translation.

PHOTOACOUSTIC IMAGE GENERATION METHOD AND APPARATUS

CROSS-REFERENCE TO RELATED APPLICATIONS

This application is a Continuation of PCT International Application No. PCT/JP2015/004415 filed on Aug. 31, 2015, which claims priority under 35 U.S.C. § 119(a) to Japanese Patent Application No. 2014-193566 filed on Sep. 24, 2014. Each of the above applications is hereby expressly incorporated by reference, in its entirety, into the present application.

BACKGROUND OF THE INVENTION

1. Field of the Invention

The present invention relates to a photoacoustic image generation method, that is, a method of emitting light toward a subject and imaging the subject based on acoustic waves generated from a part of the subject that has received the light, in particular, a method of imaging the subject in a three-dimensional manner.

In addition, the present invention relates to an apparatus for implementing such a photoacoustic image generation method.

2. Description of the Related Art

As conventionally disclosed in, for example, JP2005-21380A and JP2011-217767A, a photoacoustic imaging apparatus for imaging the inside of a living body using the photoacoustic effect has been known. In this photoacoustic imaging apparatus, pulsed light, such as pulsed laser light, is emitted to the living body. Inside the living body to which the pulsed light has been emitted, the volume of the living tissue that has absorbed the energy of the pulsed light increases due to heat, and acoustic waves are generated. Therefore, it is possible to detect the acoustic waves (photoacoustic waves) using detection means, such as an ultrasound probe, and visualize the inside of the living body based on the electrical signal (photoacoustic signal) obtained by the detection.

Since the photoacoustic imaging apparatus forms an image based only on the photoacoustic waves emitted from a specific light absorber, the photoacoustic imaging apparatus is suitable for imaging a specific tissue in the living body, for example, a blood vessel. JP2012-231879A has proposed to construct and display a three-dimensional photoacoustic image from image data including a plurality of two-dimensional photoacoustic images. In particular, it is difficult to observe fine and three-dimensional intricate tissues, such as blood vessels, on a two-dimensional photoacoustic image. However, such tissues are displayed so as to be easy to observe in a three-dimensional photoacoustic image.

Incidentally, in a known photoacoustic imaging apparatus, light emitted toward a subject may be multi-reflected by the observation target tissue or the like inside the subject, or may be reflected by tissues or the like other than the observation target. For this reason, photoacoustic waves generated from a part inside the subject that has received the reflected light are detected later than photoacoustic waves emitted by the observation target tissue, which are to be detected originally. Accordingly, there is a problem that artifacts are caused in the photoacoustic image.

In addition, photoacoustic waves generated from a part inside the subject are reflected at a boundary between bone and tissue or on the probe surface, and the reflected waves are further reflected by a part (a place that is not necessarily the same as the part where the photoacoustic waves have been generated) inside the subject. That is, multi-reflection occurs. Accordingly, there is a problem that artifacts are caused in the photoacoustic image.

JP2013-188310A discloses distinguishing a two-dimensional photoacoustic image showing an observation target part from a two-dimensional photoacoustic image based on the artifacts described above and displaying these images on one image display device side by side or with a time difference therebetween.

SUMMARY OF THE INVENTION

However, even if the two-dimensional photoacoustic image without artifacts is displayed as shown in JP2013-188310A, the problem that it is difficult to observe fine and three-dimensional intricate tissues, such as blood vessels, on the two-dimensional photoacoustic image still remains.

The present invention has been made in view of the aforementioned situation, and it is an object of the present invention to provide a method capable of generating a photoacoustic image in which artifacts are reduced and fine and three-dimensional intricate tissues, such as blood vessels, can also be easily observed.

In addition, it is an object of the present invention to provide a photoacoustic image generation apparatus capable of implementing such a photoacoustic image generation method.

A photoacoustic image generation method according to the present invention is a photoacoustic image generation method for obtaining a photoacoustic signal by emitting light toward a subject from a light source and detecting photoacoustic waves emitted from the subject having received the light and imaging the subject based on the photoacoustic signal. The photoacoustic image generation method includes: generating photoacoustic images relevant to a plurality of cross sections of the subject by changing an angle between a surface of the subject and an emission direction of the light; removing a signal showing a component appearing discontinuously in the subject from photoacoustic signals showing the plurality of cross sections; and generating a three-dimensional image of the subject from photoacoustic signals showing the plurality of cross sections after the removal processing.

In the photoacoustic image generation method according to the present invention, it is preferable that a probe that performs emission of the light and detection of the photoacoustic waves for each cross section of the subject is used and the angle is changed by changing a direction of the probe.

In the photoacoustic image generation method of the present invention, it is preferable that a surface of the probe on a light emission side is brought into contact with the surface of the subject and that the angle is changed by swinging the probe around an axis extending along the surface of the subject included in one of the cross sections.

In the case of changing the angle as described above, it is preferable to attach an angle sensor to the probe and detect the angle by the angle sensor.

On the other hand, a photoacoustic image generation apparatus according to the present invention is a photoacoustic image generation apparatus for obtaining a photoacoustic signal by emitting light toward a subject from a light source and detecting photoacoustic waves emitted from the subject having received the light and imaging the subject based on the photoacoustic signal. The photoacoustic image generation apparatus has: means for removing a signal showing a component appearing discontinuously in the subject from photoacoustic signals relevant to a plurality of cross sections of the subject that have been generated by changing an angle between a surface of the subject and an emission direction of the light; and means for constructing a three-dimensional image of the subject from photoacoustic signals showing the plurality of cross sections after the removal processing.

In the photoacoustic image generation apparatus of the present invention, it is preferable to further provide light source angle changing means for changing a direction of the light source with respect to the subject in order to change the angle between the surface of the subject and the emission direction of the light.

In the photoacoustic image generation apparatus according to the present invention, it is preferable that a probe that performs emission of the light and detection of the photoacoustic waves for each cross section of the subject is provided and the light source angle changing means changes the direction of the probe.

It is preferable that the light source angle changing means swings the probe, of which a surface on a light emission side is in contact with the surface of the subject, around an axis extending along the surface of the subject included in one of the cross sections.

In a case where the light source angle changing means has the configuration described above, it is preferable that an angle sensor for detecting the angle is attached to the probe.

According to the photoacoustic image generation method of the present invention, a signal showing a component appearing discontinuously in the subject is removed from photoacoustic signals showing a plurality of cross-sections, and a three-dimensional image of the subject is generated from photoacoustic signals showing the plurality of cross sections after the removal processing. Therefore, it is possible to generate a three-dimensional photoacoustic image in which artifacts are reduced or absent and fine and three-dimensional intricate tissues, such as blood vessels, can be easily observed.

On the other hand, the photoacoustic image generation apparatus of the present invention is a photoacoustic image generation apparatus for obtaining a photoacoustic signal by emitting light toward the subject from the light source and detecting photoacoustic waves emitted from the subject having received the light and imaging the subject based on the photoacoustic signal. Since the photoacoustic image generation apparatus has the means for removing a signal showing a component appearing discontinuously in the subject from photoacoustic signals relevant to a plurality of cross sections of the subject that have been generated by changing an angle between a surface of the subject and an emission direction of the light and the means for constructing a three-dimensional image of the subject from photoacoustic signals showing the plurality of cross sections after the removal processing, it is possible to implement the photoacoustic image generation method of the present invention described above.

DESCRIPTION OF THE PREFERRED EMBODIMENTS

Figure 1:
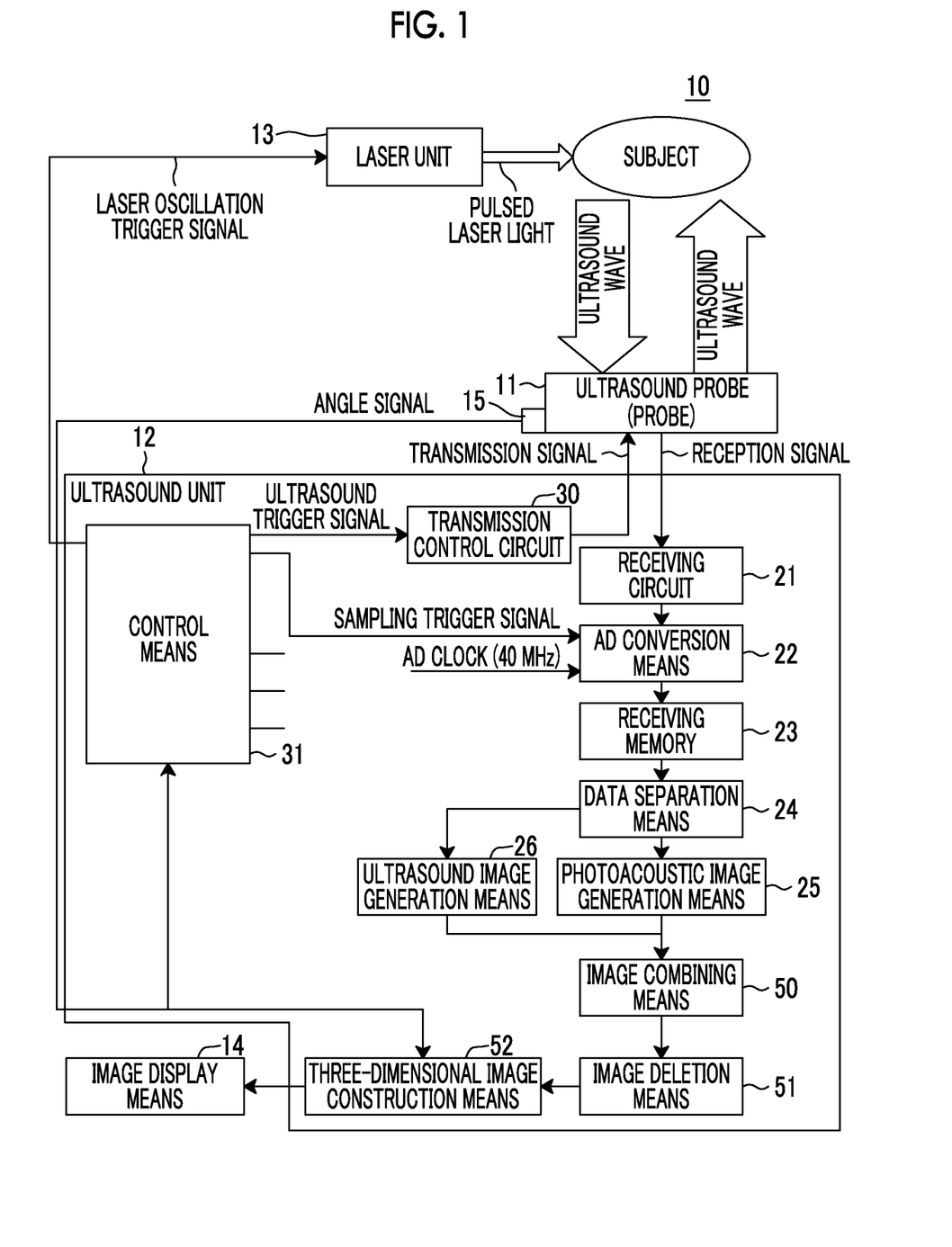
FIG. 1 is a block diagram showing the schematic configuration of a photoacoustic image generation apparatus according to an embodiment of the present invention.

Hereinafter, embodiments of the present invention will be described in detail with reference to the diagrams. FIG. 1 is a block diagram showing the basic configuration of a photoacoustic image generation apparatus 10 according to a first embodiment of the present invention. The photoacoustic image generation apparatus 10 can generate both a photoacoustic image and an ultrasound image, and includes an ultrasound probe (probe) 11, an ultrasound unit 12, a laser unit 13, and image display means 14.

As the laser unit 13, for example, a laser unit that emits laser light having a center wavelength of 756 nm is applied. From the laser unit 13, pulsed laser light (hereinafter, simply referred to as laser light) is emitted toward a subject. Although the path of the laser light is schematically shown in FIG. 1, it is desirable that the laser light is guided to the probe 11 using guiding means, such as a plurality of optical fibers, and is emitted toward the subject from a portion of the probe 11. The following explanation will be given on the assumption that light is emitted as described above.

The probe 11 performs output (transmission) of ultrasound waves to a subject to be examined, as a subject, and detection (reception) of reflected ultrasound waves that are reflected back from the subject. Therefore, the probe 11 has a plurality of ultrasound transducers arranged in a one-dimensional manner, for example. The probe 11 detects photoacoustic waves, which are generated when an observation part in the subject absorbs the laser light from the laser unit 13, with the plurality of ultrasound transducers. The probe 11 detects the photoacoustic waves and outputs a photoacoustic wave detection signal, and detects the reflected ultrasound waves (reflected acoustic waves) and outputs an ultrasound detection signal.

In a case where the guiding means described above is coupled to the probe 11, an end portion of the guiding means, that is, distal end portions of a plurality of optical fibers or the like are arranged along the arrangement direction of the plurality of ultrasound transducers. From the distal end portions, laser light is emitted toward the subject. Hereinafter, the case where the guiding means is coupled to the probe 11 as described above will be described as an example.

When generating a photoacoustic image or an ultrasound image (reflected acoustic wave image) of the subject, the probe 11 is moved in a direction approximately perpendicular to the one-dimensional direction in which a plurality of ultrasound transducers are arranged, or the probe 11 is swung as will be described later. Accordingly, the subject is scanned in a two-dimensional manner with the laser light and the ultrasound waves. This scan may be performed by an examiner who manually moves the probe 11, or a more precise two-dimensional scan may be realized using a scanning mechanism.

In addition, an angle sensor 15 for detecting the angle of the probe 11 at the time of swinging is attached to the probe 11. The angle of the probe 11 will be described in detail later.

Instead of the ultrasound waves described above, acoustic waves having audible frequencies may be used to generate an image based on the reflected acoustic waves.

The ultrasound unit 12 has a receiving circuit 21, AD conversion means 22, a receiving memory 23, data separation means 24, photoacoustic image generation means 25, ultrasound image generation means 26. The output of the photoacoustic image generation means 25 is input to the image display means 14, which is formed by using, for example, a CRT or a liquid crystal display device, through image combining means 50 to be described later. In addition, the ultrasound unit 12 has a transmission control circuit 30, control means 31 for controlling the operation of each section in the ultrasound unit 12, the image combining means 50, and image deletion means 51.

The receiving circuit 21 receives the photoacoustic wave detection signal and the ultrasound detection signal output from the probe 11. The AD conversion means 22 is sampling means, and samples the photoacoustic wave detection signal and the ultrasound detection signal received by the receiving circuit 21 and converts the photoacoustic wave detection signal and the ultrasound detection signal into photoacoustic data and ultrasound data that are digital signals. This sampling is performed at predetermined sampling periods in synchronization with an AD clock signal. The receiving circuit 21 may be configured to include the AD conversion means 22.

The laser unit 13 is configured to include a Ti:Sapphire laser, an optical parametric oscillation (OPO) laser based on the second harmonic excitation of a YAG laser, a Q-switch pulsed laser formed of an alexandrite laser, or the like. A laser oscillation trigger signal instructing the emission of light is input to the laser unit 13 from the control means 31. When the laser oscillation trigger signal is received, the laser unit 13 emits pulsed laser light having a wavelength of 756 nm. In addition, the laser unit 13 may be formed of other semiconductor lasers, for example.

The control means 31 inputs an ultrasound trigger signal instructing the transmission of ultrasound waves to the transmission control circuit 30. When the ultrasound trigger signal is received, the transmission control circuit 30 makes the probe 11 transmit ultrasound waves. The control means 31 outputs the laser oscillation trigger signal first, and then outputs the ultrasound trigger signal. Emission of laser light toward the subject in response to the output of the laser oscillation trigger signal and detection of photoacoustic waves are performed, and then transmission of ultrasound waves to the subject in response to the output of the ultrasound trigger signal and detection of reflected ultrasound waves are performed.

The control means 31 further outputs a sampling trigger signal instructing the start of sampling to the AD conversion means 22. The sampling trigger signal is output after the laser oscillation trigger signal is output and before the ultrasound trigger signal is output, more preferably, at a timing at which laser light is actually emitted toward the subject. Therefore, the sampling trigger signal is output in synchronization with a timing at which the control means 31 outputs the laser oscillation trigger signal, for example. In response to the reception of the sampling trigger signal, the AD conversion means 22 starts the sampling of the photoacoustic wave detection signal that is received by the receiving circuit 21 after being output from the probe 11.

The control means 31 outputs the ultrasound trigger signal at a timing, at which the detection of photoacoustic waves is ended, after outputting the laser oscillation trigger signal. At this time, the AD conversion means 22 continues the sampling without interrupting the sampling of a photoacoustic wave detection signal. In other words, the control means 31 outputs an ultrasound trigger signal in a state in which the AD conversion means 22 continues to sample the photoacoustic wave detection signal. In response to the ultrasound trigger signal, the probe 11 transmits ultrasound waves. Then, the detection target of the probe 11 is changed to reflected ultrasound waves from the photoacoustic waves. The AD conversion means 22 continuously samples the photoacoustic wave detection signal and the ultrasound detection signal by continuously sampling the detected ultrasound detection signal. The ultrasound trigger signal may be output after the AD conversion means 22 stops sampling the photoacoustic wave detection signal.

The AD conversion means 22 stores the photoacoustic data and the ultrasound data obtained by sampling in the common receiving memory 23. The sampling data stored in the receiving memory 23 is photoacoustic data up to a certain point in time, and is ultrasound data after the certain point in time. The data separation means 24 separates the photoacoustic data and the ultrasound data, which are stored in the receiving memory 23, from each other.

Hereinafter, generation and display of a photoacoustic image and an ultrasound image will be described. The ultrasound data and the photoacoustic data read from the receiving memory 23 are input to the data separation means 24 shown in FIG. 1. The data separation means 24 inputs only the photoacoustic data to the photoacoustic image generation means 25 at the subsequent stage when generating a photoacoustic image. Based on the photoacoustic data, the photoacoustic image generation means 25 generates a photoacoustic image relevant to the scanning surface (scanning cross section) scanned with the laser light. Here, the photoacoustic image is generated by processing including, for example, image reconstruction such as phase matching addition, detection, and logarithmic conversion.

The photoacoustic image generation apparatus 10 of the present embodiment can display a two-dimensional photoacoustic image relevant to one of the scanning surfaces, and can generate and display a three-dimensional image of the subject based on photoacoustic images relevant to a plurality of scanning surfaces. In the case of displaying a two-dimensional photoacoustic image, data indicating the photoacoustic image generated by the photoacoustic image generation means 25 is input to the image display means 14 through the image deletion means 51 and three-dimensional image construction means 52 after combining processing, which will be described later, is performed as necessary by the image combining means 50. As a result, the two-dimensional photoacoustic image of the subject relevant to the scanning surface is displayed on the image display means 14.

On the other hand, in the case of displaying a three-dimensional photoacoustic image, data indicating the photoacoustic image generated by the photoacoustic image generation means 25 is input to the three-dimensional image construction means 52 after the combining processing, which will be described later, is performed as necessary by the image combining means 50 and then deletion processing, which will be described later, is performed by the image deletion means 51. The three-dimensional image construction means 52 constructs a three-dimensional photoacoustic image of the subject based on data indicating photoacoustic images relevant to a plurality of different scanning surfaces, and inputs image data indicating the constructed image to the image display means 14. As a result, the three-dimensional photoacoustic image of the subject is displayed on the image display means 14.

The data separation means 24 inputs only the ultrasound data to the ultrasound image generation means 26 at the subsequent stage when generating an ultrasound image. The ultrasound image generation means 26 generates an ultrasound image relevant to the scanning surface, which is scanned with ultrasound waves, based on the ultrasound data. The ultrasound image is also generated by processing including, for example, image reconstruction such as phase matching addition, detection, and logarithmic conversion.

The ultrasound image generated by the ultrasound image generation means 26 can be displayed in combination with the photoacoustic image, and or can be displayed alone. In the former case, image data indicating an ultrasound image is combined with the image data indicating the photoacoustic image by the image combining means 50. Accordingly, the ultrasound image is displayed on the image display means 14 so as to, for example, be superimposed on the two-dimensional or three-dimensional photoacoustic image described above. In the latter case, image data indicating an ultrasound image is input to the image display means 14 through the image combining means 50, the image deletion means 51, and the three-dimensional image construction means 52. Accordingly, the ultrasound image is displayed alone on the image display means 14.

Figure 2:
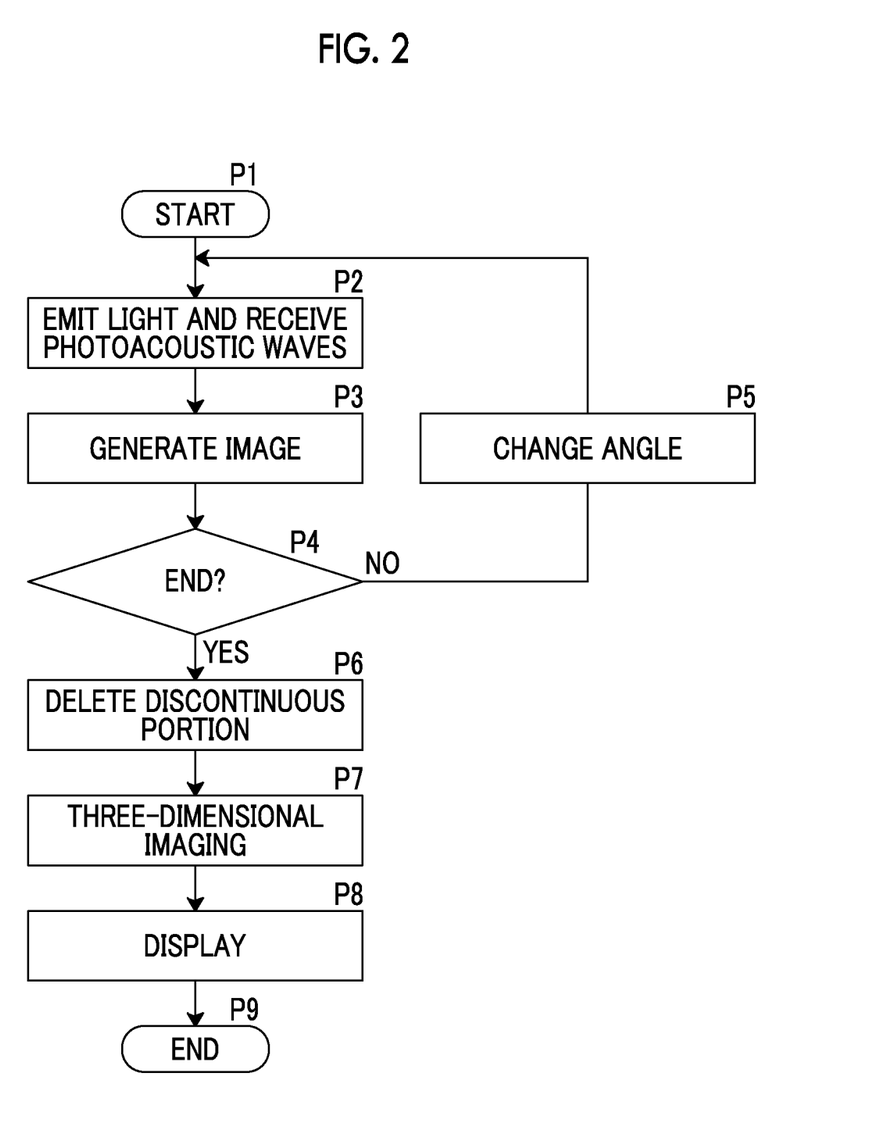
FIG. 2 is a flowchart showing a three-dimensional image generation process performed in the apparatus shown in FIG. 1.

Here, a process of generating and displaying a three-dimensional photoacoustic image will be described in detail with reference to FIGS. 2 to 5. A flowchart shown in FIG. 2 shows the flow of this process in which a part of the control is performed by the control means 31 shown in FIG. 1, for example. As shown in FIG. 2, this process starts in step P1. Then, in step P2, the transmission of laser light and the reception of photoacoustic waves described above are performed. Then, in step P3, a photoacoustic image is generated by the photoacoustic image generation means 25.

After the generation of a photoacoustic image, in step P4, it is determined whether or not the generation of a photoacoustic image has been performed a predetermined number of times (n times). That is, in the case of generating the three-dimensional photoacoustic image, whenever the probe 11 is swung to change the angle as described above, the generation of a photoacoustic image is performed once by the photoacoustic image generation means 25 (that is, one two-dimensional photoacoustic image is generated). In step P4, it is determined whether or not the number of times of the generation has reached n.

Figure 3:
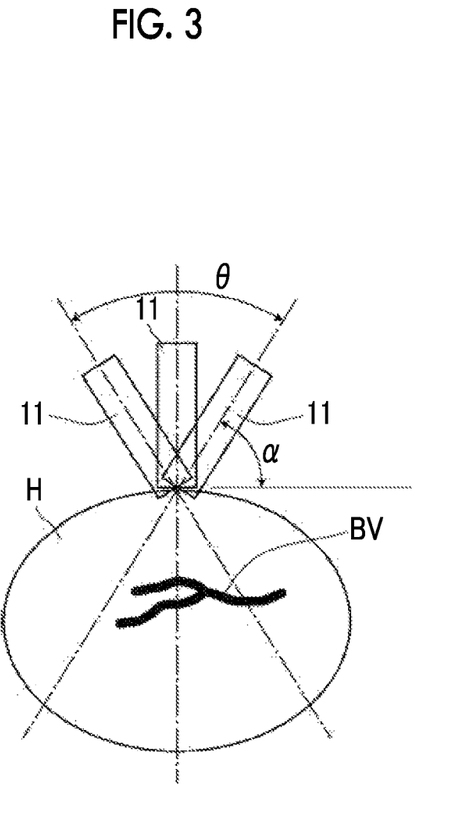
FIG. 3 is a schematic diagram showing the situation of subject imaging performed in the apparatus shown in FIG. 1.

Here, the swinging of the probe 11 will be described with reference to FIG. 3. In FIG. 3, for example, a subject to be examined (a subject) including a blood vessel BV is shown as H, and only three directions of the probe 11 with respect to the subject H are shown. Although not shown in FIG. 3 in order to avoid complication, the angle sensor 15 is attached to the probe 11 shown in FIG. 1. As shown in FIG. 3, the probe 11 is used to transmit laser light and receive photoacoustic waves in a state in which a surface (a lower end surface in the drawing) of the probe 11 on the light emission side is in contact with the surface of the subject H. The one-dimensional arrangement direction of a plurality of ultrasound transducers in the probe 11 is a direction perpendicular to the plane shown in FIG. 3. Accordingly, the generation of a photoacoustic image of each time is performed for each cross section perpendicular to the plane shown in FIG. 3, which includes the center axis (indicated by one-dot chain line) of the probe 11. That is, each two-dimensional photoacoustic image is a tomographic image relevant to the cross section.

As shown in FIG. 3, the swinging of the probe 11 is performed around an axis extending along the surface of the subject H, which is included in the cross section, over an angle range $\theta$. Then, whenever the swing position of the probe 11 is changed in the angle range $\theta$, that is, whenever an angle $\alpha$ between the surface of the subject H and the light emission direction is changed by a certain pitch angle $\Delta\alpha$, transmission of laser light and reception of photoacoustic waves are performed. The pitch angle $\Delta\alpha$ is determined in advance as an appropriate value based on the angle range $\theta$ and the number (=n) of two-dimensional photoacoustic images required when constructing a three-dimensional photoacoustic image.

In the present embodiment, swinging of the probe 11 is made by manual operation of an examiner, for example. In this case, it is difficult to make the pitch angle $\Delta\alpha$ strictly constant. However, if the angle of the probe 11 when a plurality of two-dimensional photoacoustic images are generated is calculated by the angle sensor 15, it is possible to normally generate a three-dimensional photoacoustic image based on these angles. In addition, it is also possible to perform the swinging of the probe 11 by automatic operation as will be described later. In this case, it becomes easy to make the pitch angle $\Delta\alpha$ of the swinging of the probe 11 strictly constant.

In a case where it is determined that the number of times of generation of a two-dimensional photoacoustic image has not reached n in step P4, the swing angle of the probe 11 is changed by the pitch angle $\Delta\alpha$ in next step P5. Generally, the generation of a two-dimensional photoacoustic image is started in a state in which the probe 11 is disposed first on the one end side of the angle range $\theta$. Then, a two-dimensional photoacoustic image is generated whenever the probe 11 is swung by the pitch angle $\Delta\alpha$ toward the other end side of the angle range $\theta$. In step P5, the angle of the probe 11 is also changed by manual operation of the examiner. However, in a case where the angle change is required, it is desirable that the control means 31 shown in FIG. 1 displays, for example, a message "please change the angle of the probe by 5° and perform the next imaging" on the image display means 14 in order to assist the operation of the examiner.

If it is determined in step P4 that the generation of a two-dimensional photoacoustic image and the change of the angle of the probe 11 have been sequentially performed and "n" two-dimensional photoacoustic images have been generated, the process proceeds to step P6. In step P6, processing for deleting a discontinuous portion in each of the "n" two-dimensional photoacoustic images, that is, processing for removing a signal, which indicates a component discontinuously appearing in the subject H, from a set of image signals indicating the "n" two-dimensional photoacoustic images is performed.

Figure 4:
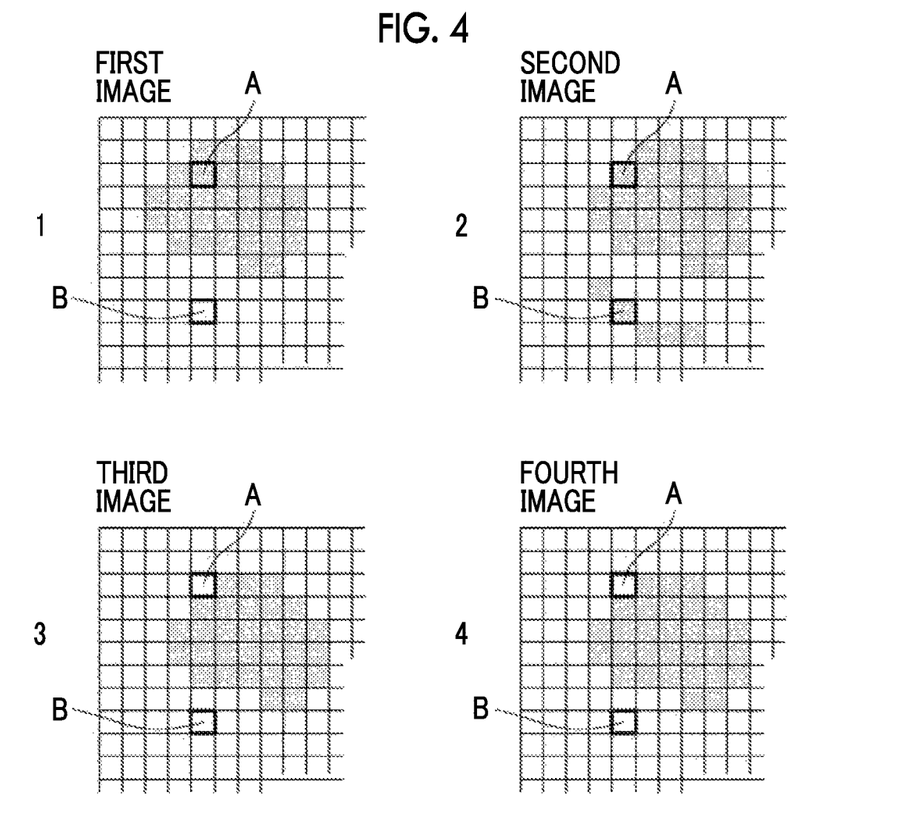
FIG. 4 is a schematic diagram illustrating image deletion performed in the apparatus shown in FIG. 1.

Hereinafter, the signal removal processing will be described with reference to FIG. 4. FIG. 4 schematically shows four two-dimensional photoacoustic images as an example that are generated by changing the angle of the probe 11 with respect to the subject surface by the pitch angle $\Delta\alpha$ as described above. More specifically, 2 of FIG. 4 is generated by changing the probe angle by $+\Delta\alpha$ with respect to the angle of the probe 11 when 1 of FIG. 4 is generated, 3 of FIG. 4 is generated by changing the probe angle by +2Δα with respect to the angle of the probe 11 when 1 of FIG. 4 is generated, and 4 of FIG. 4 is generated by changing the probe angle by +3Δα with respect to the angle of the probe 11 when 1 of FIG. 4 is generated. Hereinafter, images shown in 1, 2, 3, and 4 of FIG. 4 are referred to as a first image, a second image, a third image, and a fourth image, respectively.

In the first to fourth images, it is assumed that one square represents one pixel and filled squares are pixels showing something with high brightness. In this example, a high-brightness portion that is configured to include 30 pixels and shows, for example, a blood vessel is shown in the upper portion of each of the first to fourth images. In the first to fourth images, a pixel A at a certain common position and a pixel B at another common position are set as pixels of interest, and an image signal for each pixel is considered. The image signal in this case is digital image data including the brightness value or the density value of each pixel. Although such digital image data is usually multi-valued data indicating gradation, it is assumed that only two values of high-brightness data and low-brightness data are taken in order to simplify the explanation. That is, image data regarding filled pixels in the diagram is assumed to be high-brightness data, and image data regarding the other pixels is assumed to be low-brightness data.

Image data regarding the pixel A is high-brightness data and continuous in both the first and second images. However, in the next third image, the image data regarding the pixel A is low-brightness data. Accordingly, the image data regarding the pixel A is discontinuous between the second and third images. In addition, image data regarding the pixel B is also discontinuous between the first and second images and between the second and third images.

Here, the high-brightness data regarding the pixel A can be regarded as indicating an object continuous in the subject if the image data regarding a plurality of pixels in the vicinity of the pixel A in the first to fourth images is referred to. Therefore, the image deletion means 51 shown in FIG. 1 does not delete the high-brightness data regarding the pixel A. In contrast, the high-brightness data regarding the pixel B indicates a component discontinuously appearing in the subject if the image data regarding a plurality of pixels in the vicinity of the pixel B in the first to fourth images is referred to. Therefore, the image deletion means 51 deletes the high-brightness data regarding the pixel B.

As described above, whether certain image data indicates an object that is continuous in the subject or a component appearing discontinuously in the subject can be determined by, for example, a method of checking whether or not there are highly correlated signals by performing comparison for each region including a pixel of interest and its neighboring pixels, such as block matching known in the related art.

As described above, it is thought that the high-brightness data indicating a component appearing discontinuously in the subject is basically due to artifacts (false image). Such artifacts are caused by the fact that laser light emitted toward the subject or photoacoustic waves generated within the subject are multi-reflected, for example, on the blood vessel to be observed or are reflected on other bones or the like. That is, since photoacoustic waves generated from a part of the subject that has received laser light after the multi-reflection or the reflection are detected by the probe 11 later than photoacoustic waves generated at the original observation target part, artifacts may be caused. Basically, such artifacts are caused only in a case where laser light is emitted in a specific direction with respect to the subject, and is not caused in a case where the laser light is emitted in the other directions.

As described above, in a case where it is determined that image data regarding a pixel of interest indicates a component appearing discontinuously in the subject based on the pixel of interest and image data of its neighboring pixels, if the image data regarding the pixel of interest is deleted, it is possible to accurately remove only image data due to artifacts. On the other hand, if continuity and discontinuity of image data between two images are simply checked and discontinuous image data is deleted, continuous extension in a scanning cross section of a specific direction occurs. As a result, image data indicating actual small tissues, which are not present in scanning cross sections of the other directions, may be deleted.

Then, in step P7 shown in FIG. 2, the image data after the deletion processing is subjected to three-dimensional processing by the three-dimensional image construction means 52 shown in FIG. 1. In the three-dimensional processing, information indicating the angle of the probe 11 that is sequentially transmitted from the angle sensor 15 when each of a plurality of two-dimensional photoacoustic images is used so as to match each two-dimensional photoacoustic image. Then, in step P8, the image data after the three-dimensional processing is transmitted to the image display means 14 shown in FIG. 1 and a three-dimensional photoacoustic image is displayed based on the image data. Then, in step P9, the series of processes are ended.

Figure 5:
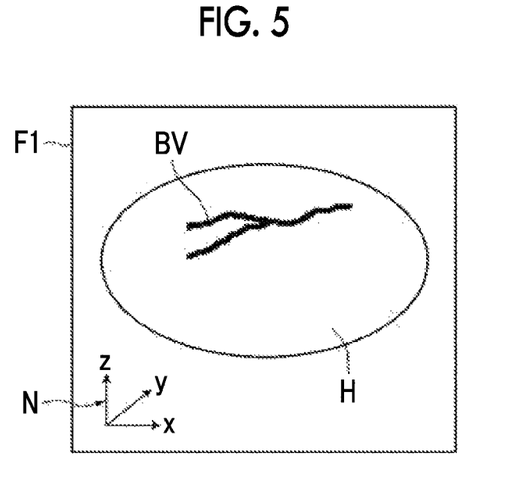
FIG. 5 is a schematic diagram showing an example of a three-dimensional image generated by a method of the present invention.

FIG. 5 schematically shows an example of the three-dimensional photoacoustic image displayed on the image display means 14 as described above. In a three-dimensional photoacoustic image F1, a three-dimensional image of the subject H including, for example, the blood vessel BV of the observation object is shown together with a display N showing the respective directions of three dimensions. Since the thin blood vessel BV has a complicated intricate shape, the complicated shape can be satisfactorily observed by displaying the blood vessel BV on a three-dimensional photoacoustic image rather than displaying it on a two-dimensional photoacoustic image.

Figure 6:
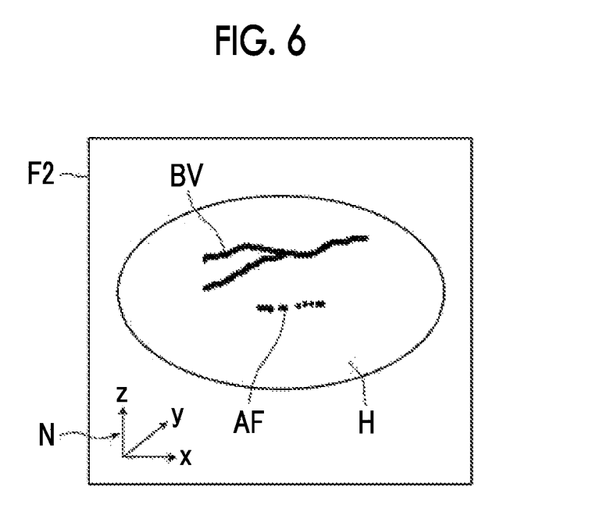
FIG. 6 is a schematic diagram showing an example of a three-dimensional image generated by a method other than the present invention.

If a three-dimensional photoacoustic image is generated and displayed using the image data indicating a plurality of two-dimensional photoacoustic images generated by the photoacoustic image generation means 25 as it is without performing the image deletion processing described above, a three-dimensional photoacoustic image F2 shown in FIG. 6 is displayed as an example. That is, in the three-dimensional photoacoustic image F2, the artifact AF described above is displayed together with the subject H.

In addition, when displaying a three-dimensional photoacoustic image on the image display means 14, a two-dimensional photoacoustic image may be displayed together therewith. The two-dimensional photoacoustic image displayed in this manner may be an image based on image data after performing the image deletion processing described above, or may be an image based on image data before performing the image deletion processing, or may be an image on which the aforementioned ultrasound image is superimposed.

Although the angle of the probe 11 is detected by the angle sensor 15 attached to the probe 11 in the embodiment described above, the angle of the probe 11 may also be detected by, for example, a magnetic sensor provided at a position different from the probe 11.

Figure 7:
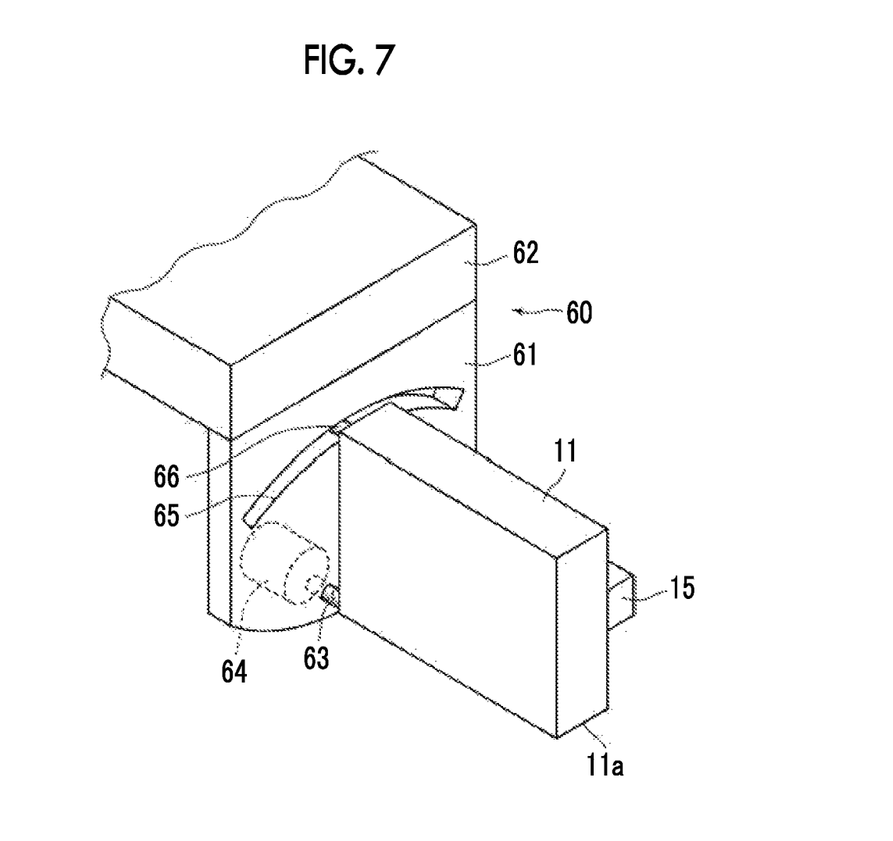
FIG. 7 is a perspective view showing a part of a photoacoustic image generation apparatus according to another embodiment of the present invention.

In the embodiment described above, the probe 11 is swung by manual operation, so that the angle (angle α shown in FIG. 3) between the emission direction of laser light and the surface of the subject is changed. However, it is also possible to change the angle automatically using light source angle changing means. FIG. 7 shows an example of such light source angle changing means 60. As shown in FIG. 7, the means is configured to include a plate-shaped probe holding plate 61 extending vertically, a connection member 62 having one end connected to the probe holding plate 61 and the other end (not shown) connected to a stand or the like on the floor, a swing shaft 63 that is connected to the side surface of the probe 11 near the surface (lower end surface in FIG. 7) of the probe 11 on the light emission side and is rotatably inserted into the probe holding plate 61, an actuator 64 for rotating the swing shaft 63, and a guide shaft 66 connected to the side surface of the probe 11 near the upper end of the probe 11.

The guide shaft 66 and the swing shaft 63 are disposed so as to extend in parallel to each other. The guide shaft 66 is inserted into an arc-shaped guide groove 65 provided in the probe holding plate 61. In addition, on the surface (lower end surface in FIG. 7) of the probe 11 on the light emission side, distal end portions (not shown) of light guide means, such as a plurality of optical fibers described previously, are arranged side by side in a direction parallel to the extension direction of the swing shaft 63. These distal end portions form a part of the light source.

In the configuration described above, it is possible to swing the probe 11 as shown in FIG. 3, that is, around the swing shaft 63 while moving the guide shaft 66 along the guide groove 65 by rotating the swing shaft 63 using the actuator 64.

What is claimed is:

1. A photoacoustic image generation method for obtaining a photoacoustic signal by emitting light toward a subject from a light source and detecting photoacoustic waves emitted from the subject having received the light and imaging the subject based on the photoacoustic signal, the method comprising:

generating photoacoustic images relevant to three or more cross sections of the subject by changing an angle between a surface of the subject and an emission direction of the light, specifying a signal showing a component appearing discontinuously in the subject based on the photoacoustic images showing the three or more cross sections;

removing the signal showing a component appearing discontinuously in the subject as a process for removing artifacts which are generated due to multiple reflections of the light from photoacoustic signals showing the three or more cross sections based on one discontinuity between a first and second image and another discontinuity between the second and third image, wherein the first, second and third images are adjacent; and generating a three-dimensional image of the subject from the photoacoustic images showing the three or more of cross sections after removal processing, wherein specifying and removing is performed by a processor.

2. The photoacoustic image generation method according to claim 1, wherein a probe that performs emission of the light and detection of the photoacoustic waves for each cross section of the subject is used; and the angle is changed by changing a direction of the probe.

3. The photoacoustic image generation method according to claim 2, wherein a surface of the probe on a light emission side is brought into contact with the surface of the subject, and the angle is changed by swinging the probe around an axis extending along the surface of the subject included in one of the cross sections.

4. The photoacoustic image generation method according to claim 3, wherein an angle sensor is attached to the probe, the angle is detected by the angle sensor, and the three-dimensional image showing the subject is generated based on the detected angle.

5. The photoacoustic image generation method according to claim 2, wherein an angle sensor is attached to the probe, the angle is detected by the angle sensor, and the three-dimensional image showing the subject is generated based on the detected angle.

* * * * *